US009393033B2

(12) United States Patent
Zerfas et al.

(10) Patent No.: US 9,393,033 B2
(45) Date of Patent: Jul. 19, 2016

(54) TISSUE AND STONE REMOVAL DEVICE AND RELATED METHODS OF USE

(71) Applicant: Boston Scientific Scimed, Inc., Maple Grove, MN (US)

(72) Inventors: Jeffrey W. Zerfas, Bloomington, IN (US); Troy Gardner, Carmel, IN (US); Christopher W. Green, Bloomington, IN (US); Jeffrey C. Smith, Poland, IN (US); Christopher L. Oskin, Grafton, MA (US); Kenneth J. Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 50 days.

(21) Appl. No.: 13/683,836

(22) Filed: Nov. 21, 2012

(65) Prior Publication Data

US 2013/0131445 A1    May 23, 2013

Related U.S. Application Data

(60) Provisional application No. 61/563,167, filed on Nov. 23, 2011.

(51) Int. Cl.
*A61B 1/00* (2006.01)
*A61B 17/22* (2006.01)
*A61B 1/06* (2006.01)
*A61B 1/018* (2006.01)
*A61B 18/22* (2006.01)
*A61B 1/12* (2006.01)
(Continued)

(52) U.S. Cl.
CPC ............... *A61B 17/22* (2013.01); *A61B 1/018* (2013.01); *A61B 1/0661* (2013.01); *A61B 18/22* (2013.01); *A61B 18/24* (2013.01); *A61B 2018/00982* (2013.01); *A61B 2090/373* (2016.02); *A61B 2218/002* (2013.01); *A61B 2218/007* (2013.01)

(58) Field of Classification Search
CPC ..... A61B 1/00087; A61B 1/015; A61B 1/018; A61F 9/008
USPC ................ 600/104, 108, 127, 129, 130, 156; 348/45; 356/241.1; 606/2.5, 46
See application file for complete search history.

(56) References Cited

U.S. PATENT DOCUMENTS

| 5,085,658 | A | | 2/1992 | Meyer | |
| 5,290,279 | A | * | 3/1994 | Bonati et al. | ............ 606/15 |

(Continued)

FOREIGN PATENT DOCUMENTS

| WO | WO 91/06271 A1 | 5/1991 |
| WO | WO 96/32895 A2 | 10/1996 |

OTHER PUBLICATIONS

Partial International Search Report for International Application No. PCT/US2012/066382, mailed Feb. 27, 2013, 6 pgs.

*Primary Examiner* — Anhtuan T Nguyen
*Assistant Examiner* — Timothy J Neal
(74) *Attorney, Agent, or Firm* — Bookoff McAndrews, PLLC

(57) ABSTRACT

Embodiments of a medical device and related methods of use are provided for extracting tissue. The device may include an elongate member having a proximal end and a distal end. Two or more channels may extend through the elongate member from the proximal end to the distal end, and a morcellating device may be included in one of the channels. In addition, one of the channels may be configured as a return channel for extracting the morcellated tissue.

17 Claims, 5 Drawing Sheets

(51) Int. Cl.
*A61B 18/24* (2006.01)
*A61B 18/00* (2006.01)

(56) References Cited

U.S. PATENT DOCUMENTS

| | | | |
|---|---|---|---|
| 5,300,087 A | 4/1994 | Knoepfler | |
| 5,304,124 A | 4/1994 | Essig et al. | |
| 5,324,282 A * | 6/1994 | Dodick | A61B 18/26 128/897 |
| 5,370,658 A * | 12/1994 | Scheller | A61B 17/2909 606/174 |
| 5,470,320 A | 11/1995 | Tiefenbrun et al. | |
| 5,919,128 A * | 7/1999 | Fitch | 600/166 |
| 6,090,103 A | 7/2000 | Hakky et al. | |
| 6,152,919 A | 11/2000 | Hakky | |
| 6,520,955 B2 | 2/2003 | Reynard | |
| 7,104,983 B2 | 9/2006 | Grasso, III et al. | |
| 2001/0056222 A1 * | 12/2001 | Rudischhauser et al. | 600/130 |
| 2002/0123744 A1 | 9/2002 | Reynard | |
| 2005/0054900 A1 * | 3/2005 | Mawn | A61F 9/007 600/156 |
| 2007/0244353 A1 * | 10/2007 | Larsen | 600/105 |
| 2009/0131940 A1 * | 5/2009 | Brunnett | A61B 17/1624 606/80 |

* cited by examiner

TISSUE AND STONE REMOVAL DEVICE AND RELATED METHODS OF USE

CROSS-REFERENCE TO RELATED APPLICATIONS

This patent application claims the benefits of priority under 35 U.S.C. §§119-120 to U.S. Provisional Application No. 61/563,167, filed on Nov. 23, 2011, for which the entirety is incorporated herein by reference.

FIELD OF THE INVENTION

Embodiments of the present disclosure relate generally to devices suitable for use in medical procedures. In particular, embodiments of the present disclosure relate to apparatus and methods for removing tissue from within a patient's body.

BACKGROUND OF THE INVENTION

Bladder obstruction, arising from enlargement of the prostate gland in males, is one of the most common disorders in urology. The prostate gland lies under the bladder and surrounds the passageway, known as the prostatic urethra, which transfers fluids from the bladder to the sphincter and ultimately outside the body through the rest of the urethra. An enlarged prostate constricts the prostatic urethra leading to a condition known as benign prostatic hyperplasia ("BPH"). BPH causes a variety of obstructive symptoms including urinary hesitancy, decreased size and force of the urinary stream, and in extreme cases, complete urinary retention, which can lead to renal failure.

To overcome these problems, the enlarged prostate may be surgically removed after severing the gland from the body. One BPH treatment, referred to as enucleation of the prostate, employs an introducer, for example, a minimally invasive device, for example, such as a cystoscope, that includes channels to insert devices, for example, an incising device, a morcellating device and extraction device. The incising device, which may include, e.g., a Holmium laser, may carve out the prostate lobes. The severed prostate tissues are generally large, and therefore, a morcellating device may be used to fragment the tissue to facilitate easier removal of the excised tissue.

Typically, morcellation of tissue is accomplished with a mechanical morcellator. Such mechanical morcellators are well-known in the art and may include multiple moving parts and relatively larger diameters. Moreover, the enucleation and morcellation procedures may be accomplished with the help of a number of other devices, such as, for example, a visual device, an irrigation device, a resecting device. Each of these devices is typically inserted into the body lumen through the introducer. Accordingly, the dimensions of the inserted devices may be constrained by the size of the cystoscope channels.

Thus, there is a need for reducing the sizes of the various tools used in such procedures so that larger tissue fragments may be removed, thereby reducing procedure time.

SUMMARY OF THE INVENTION

Embodiments of the present disclosure provide a medical device for extracting tissue from a body.

In accordance with an aspect of the present disclosure, the medical device may include an elongate member having a proximal end and a distal end. Two or more channels may extend from the proximal end to the distal end, and a morcellating device may be carried in one of the channels. In addition, one of the channels may be configured as a return channel, configured for extracting the morcellated tissue.

In various embodiments, the device may include one or more of the following additional features: the elongate member may be flexible; the elongate member may be rigid; the morcellating device may be a laser fiber secured in the return channel; the return channel may further include a metallic tip to secure to a distal end of the return channel; the distal end of the elongate member may include a metallic tip; the tip may include a lumen having an inner diameter smaller than that of an inner diameter of the return channel; the laser fiber may be secured to an inner surface of the metallic tip with a resin that occupies a portion of an inner diameter of the tip; the return channel may be connected to a suction device; the return channel may be tapered at the distal end; a visualization device may be carried in one of the channels; and a light source may be carried in one of the channels.

In accordance with another aspect of the present disclosure, an apparatus for extracting tissue may include an elongate member having a proximal end and a distal end. Two or more channels may extend from the proximal end to the distal end. The channels may include differing configurations. A laser fiber configured to morcellate tissue may be carried in one of the channels. A visualization device configured to observe the tissue may be carried in another channel, and a light source configured to illuminate the tissue may be carried in one of the channels. In addition, one of the channels may be configured as a return channel, configured for extracting the morcellated tissue.

In various embodiments, the apparatus may include one or more of the following additional features: the return channel may be connected to a suction device for extracting morcellated tissue; the distal end of the elongate member may include a rigid tip; the laser fiber may be carried in the return channel; the laser fiber may be secured to an inner surface of the rigid tip with a resin that occupies a portion of an inner diameter of the tip; and an irrigation system may also be carried in one of the channels.

A further aspect of the present disclosure includes a method for extracting tissue. The method may include advancing a retrieval device to a location adjacent target tissue. The retrieval device may include an elongate member having a proximal end and a distal end. Two or more channels may extend from the proximal end to the distal end. The retrieval device may also include a morcellating device configured to morcellate tissue. One of the channels may be configured as a return channel, sized for extracting the morcellated tissue. The method may also include illuminating the target tissue using a light source associated with one of the channels, and viewing the target tissue with a visualization device. Further, the method may also include morcellating the target tissue and extracting the morcellated tissue.

In an embodiment, the method may further include irrigating the tissue using an irrigating system connected to the proximal end opening of one of the channels.

Additional objects and advantages of the claimed invention will be set forth in part in the description that follows, and in part will be obvious from the description, or may be learned by practice of the invention. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the present disclosure and together with the description, serve to explain the principles of the embodiments disclosed herein.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts.

Overview

The present disclosure relates generally to a retrieval device for removing an undesirable mass from a body. The retrieval device may excise and morcellate an undesirable mass into smaller pieces, illuminate the surgical site, provide a means to view the surgical site, and extract the pieces from the body. To this end, the retrieval device may include an elongate tube having one or more lumens or working channels. It should be understood that the retrieval device may be configured for use with a number of medical devices to accomplish tissue removal. For example, the retrieval device may include a visual device, an irrigation source, a light source, a morcellating device, a suction device, or any other suitable device. Such devices may be integrally formed with the retrieval device and/or one or more devices may be removably disposed within a channel of the retrieval device or coupled to the retrieval device.

Conventionally, a tissue removal process may be performed by inserting various medical devices through channels of a minimally invasive device such as, e.g., an endoscope, a cystoscope, or any other suitable introduction sheath. With this implementation, the return channel to withdraw undesired mass may be constrained by the size of the introducer's channels. As opposed to the conventional system, the retrieval device according to embodiments of the present disclosure may employ a single elongate tube having multiple lumens for accommodating the required medical devices. The size and the number of lumens may be modified to suit the requirements. For example, the return lumen may have the largest cross-sectional diameter, promoting extraction of larger tissue fragments.

Although exemplary embodiments of the present disclosure are described with reference to prostatectomy, it will be appreciated that aspects of the present disclosure have wide application. Embodiments of the present disclosure can be used for a variety of therapeutic procedures, including ureteroscopy, hysteroscopy, and cystoscopy, for example. The disclosed devices and techniques may be suitable to remove any body part or other mass. For example, the retrieval device may be utilized to remove tissue or bladder stones. Accordingly, the following descriptions and illustrations should be considered illustrative in nature, and not limit the scope of the claimed invention.

Exemplary Embodiments

Figure 1:
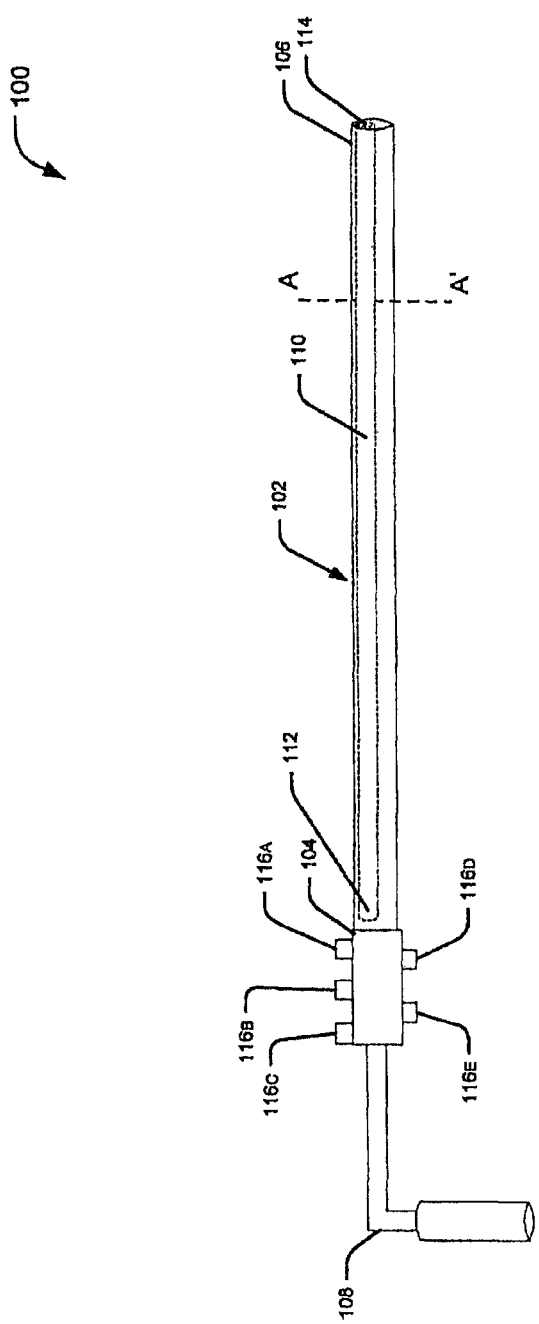
FIG. 1 is a schematic view of a retrieval device, according to an exemplary embodiment of the present disclosure.

FIG. 1 provides a schematic view of an exemplary embodiment of a retrieval device 100 for resecting an undesired mass through an incision or a natural body opening. Retrieval device 100 may include a tube 102 having a proximal end 104 and a distal end 106, and a handle 108 coupled to proximal end 104. Tube 102 may include two or more internal channels 110 having proximal and distal end openings 112, 114, respectively, to receive, e.g., one or more medical devices. The channels may be used for, among other things, providing irrigation, suction, and/or insufflation. It will be understood that "proximal" and "distal", as used in this disclosure, refer to positions or directions nearer to or farther from the user, respectively.

Tube 102 may be advanced into a natural orifice and/or an incision at a surgical site in a patient. Tube 102 may be substantially hollow, with a cross-sectional configuration adapted to be received in a desired body lumen. In the illustrated embodiment, e.g., tube 102 is generally circular, with a generally circular hollow interior lumen. Further, the tube 102 may have a uniform diameter or may taper at its distal end 106 to allow convenient insertion into the body. In another embodiment, the cross-sectional dimensions and/or configurations of tube 102 may vary along its length, as desired. For example, a proximal portion of tube 102 may include a hexagonal cross-sectional configuration while a distal portion of tube 102 may include a rectangular cross-sectional configuration, based on the intended use and application. In addition, tube 102 may be transparent or translucent, allowing an operator to view an evacuated mass within tube 102. Although tube 102 extends from handle 108 in FIG. 1, tube 102 may be configured for use without handle 108 during a portion or all of a surgical procedure.

Depending upon the particular implementation and intended use, the length of tube 102 may vary. For example, the length of tube 102 may be relatively longer for procedures within longer cavities or deeper organs, such as the bowel or intestine, or may be shorter. Similarly, depending upon the particular implementation and intended use, tube 102 can be rigid along a portion of its length, flexible along a portion of its length, or configured for flexure at only certain, specified locations.

Proximal end 104 of tube 102 may be coupled to handle 108 for gripping by an operator, such as a surgeon, while distal end 106 may remain open to allow medical devices to extend out from tube 102. Handle 108 may be attached to tube 102 by any suitable means, including, for example, welding, or adhesives, or may be integrally formed with tube 102.

Tube 102 may be made of any suitable material, for example, materials that are compatible with living tissue or a living system. That is, tube 102 may be non-toxic or non-injurious, for example, not causing an immunological reaction or rejection. Suitable materials may include nitinol, ePTFE, fabric, and suitable nickel and titanium alloys, for example.

Tube 102 may be flexible, or adapted for flexible steering within bodily lumens, as understood in the art. In such implementations, tube 102 may be a flexible sheath, surrounding channels 110, made of fiber or wires that may be woven or braided together. Suitable flexible materials may include synthetic plastics, fiber, or polymers, for example. In addition, tube 102 may include any known additional steering mechanism to allow tube maneuver. Exemplary steering mechanisms may include pull wires connected to a distal end of tube 102 and extending up to the proximal end. For steering purposes, the pull wires may be controlled at the proximal end either automatically or manually. Alternatively, tube 102 may be rigid or semi-rigid and may be made of any suitable materials, e.g., stainless steel or shape memory alloys such as nitinol.

Figure 2:
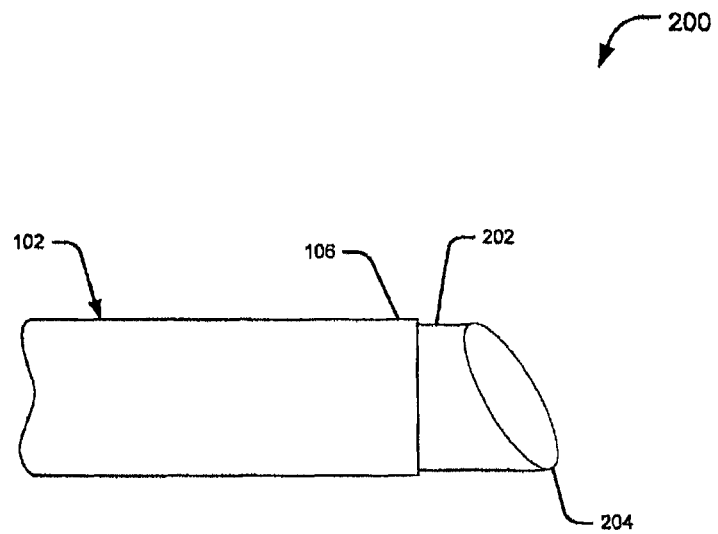
FIG. 2 depicts the distal end of the retrieval device according to the embodiment of FIG. 1.

To impart stability to flexible tube 102, distal end 106 may be connected to a rigid, hollow tip. FIG. 2 illustrates an embodiment of distal end 106 of tube 102. As shown, distal end 106 may be connected to a rigid tip 202, which may be generally cylindrical and made of a rigid material, such as stainless steel. Tip 202 may be a generally circular, hollow structure having a diameter substantially similar to that of tube 102. In one embodiment, tip 202 may include a diameter smaller than that of tube 102, so that tip 202 may be received within tube 102. In one embodiment, tip 202 may include a larger diameter so that the distal end of tube 102 may be received in tip 202. In some embodiments, tip 202 and tube 102 may be dimensioned so that the two device are secured to each other. Further, tip 202 may taper towards a narrower distal end opening, allowing only a particular-sized mass to enter tube 102. In addition, distal end 204 of tip 202 may be cut on a slant or an angle, other than perpendicular, to the longitudinal axis of tube 102. The illustrated embodiment depicts this slant distal end 204 in a side view of tip 202.

Tip 202 may be connected to tube 102 by any known securing mechanism, such as, e.g., glue or sealant. Additionally, the outer surface of tip 202 and inner surface of tube 102 may include projections, grooves, screws, or similar members that provide a snap-fit attachment between the two devices. In an alternate embodiment, tip 202 may be integrally formed with tube 102.

Tube 102 and tip 202 may be designed to impose minimum risk to the surrounding tissues while in use. To this end, proximal end 104, distal end 106, and/or tip edges may include geometrical structures, such as rounded or beveled terminal ends and/or faces, to reduce trauma and irritation to surrounding tissues. Further, the outer surface of tube 102, including tip 202, may include any suitable coating and/or covering, such as a layer of lubricous material, to facilitate insertion into a body lumen or surgical insertion.

In addition, one or more portions of tube 102 may include radiopaque or sonoreflective markings. That result can be accomplished by any of suitable conventional techniques, such as, e.g., inclusion of barium sulfate in plastic material or inclusion of one or more metal portions. These markings can be added to the exterior surface of tube 102 to detect the position and orientation of retrieval device 100 within the patient's body. A surgeon, with the aid of suitable imaging equipment, may view these markings to enable optimal positioning of retrieval device 100 to avoid potential damage to sensitive tissues.

The outer surface of tube 102 may also include geometrical structures (not shown) that may act as anchoring mechanisms. These geometrical structures may include hooks, barbs, or spikes that may assist in engaging tube 102 with the surrounding tissues, once deployed. The geometrical structures may be deployed at distal end 106, or they may be positioned along the length of tube 102.

In an alternative embodiment, tube 102 may be made of a self-expandable or compressible device that changes state during use. For example, tube 102 may be compressed to reduce its overall diameter, allowing insertion into relatively smaller body lumens, such as those in a patient's urethra. In the expanded configuration, tube 102 may expand in a radial direction. The expanded state may allow inclusion of multiple medical devices. Expansion and/or compression of tube 102 may be achieved by incorporating one or more expansion mechanisms, e.g., springs, baskets, or coil structures, within tube 102. In an embodiment, tube 102 may be made of shape memory material, such as Nitinol, that changes state upon exposure to a trigger.

Tube 102 may be adapted to receive multiple medical devices. To this end, proximal end 104 of tube 102 may include multiple ports 116a, 116b, 116c, 116d, and 116e, collectively referred to as ports 116. Each of ports 116 may connect to an internal channel, and a device advancing into port 116 may extend from distal end 106 of tube 102 via the connected channel. "Port" may refer to the proximal end opening of channel 110, or it may be an additional opening attaching the tube's proximal end 104 to channel's proximal end opening 112. Alternatively, proximal end 104 of tube 102 may be open to insert devices into channels 110 directly.

In general, the number of ports 116 may correspond to the number of channels 110 within tube 102. Alternatively, the number of ports 116 may be greater or less than the number of channels 110.

Tube 102 may include multiple channels 110 to slidingly receive two or more devices, either independently or simultaneously. Each channel may be configured to slidingly receive at least one medical device through the corresponding port 116. In general, channels 110 may be hollow, elongate structures extending from proximal end 104 to distal end 106. The following section describes these channels in greater detail.

In an alternate embodiment, tube 102 may itself receive incoming medical devices to perform the required procedures, including, for example a laser fiber to morcellate a tissue. These devices may be held in place by attaching them to tip 202 or the inner surface of tube 102, for example. In this embodiment, the fiber may be introduced through tube 102 and may be connected to tip 202 using a resin.

Figure 3A:
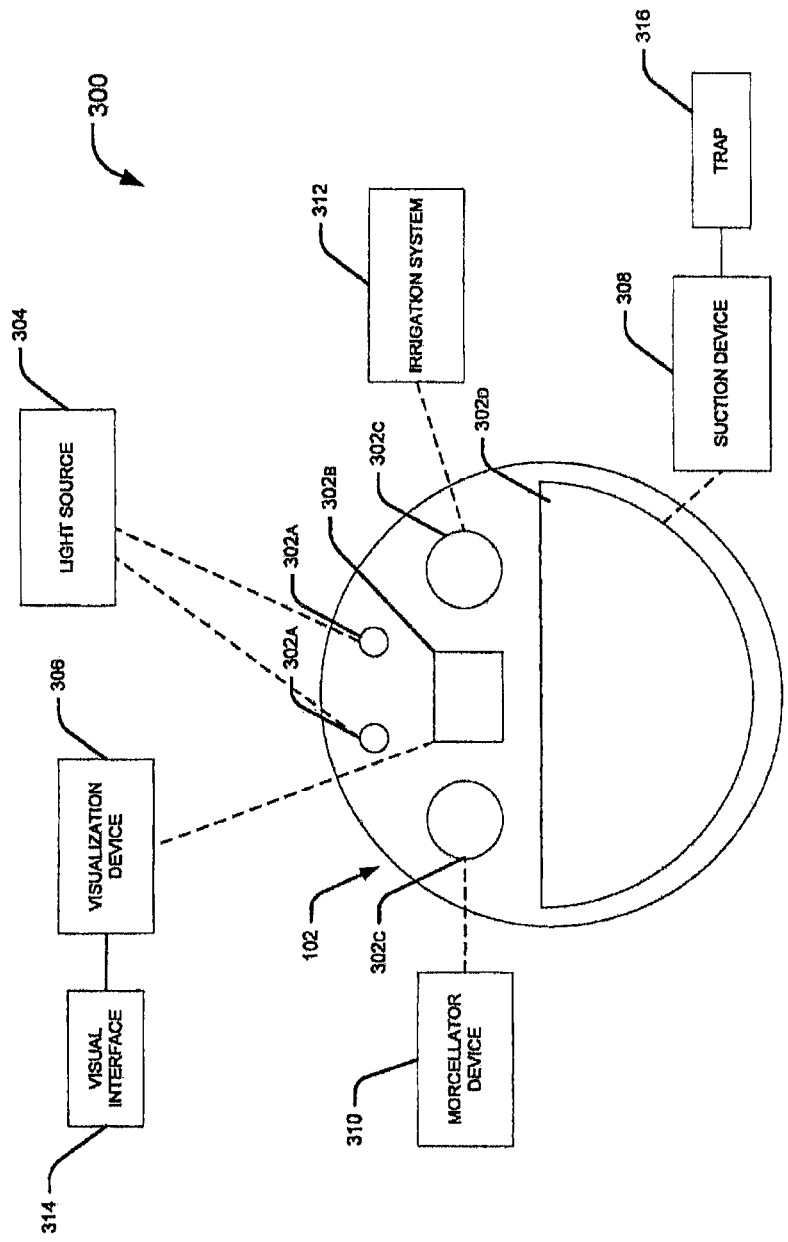
FIG. 3A is a cross-sectional view of the retrieval device shown in FIG. 1, taken along plane A-A.
Figure 3B:
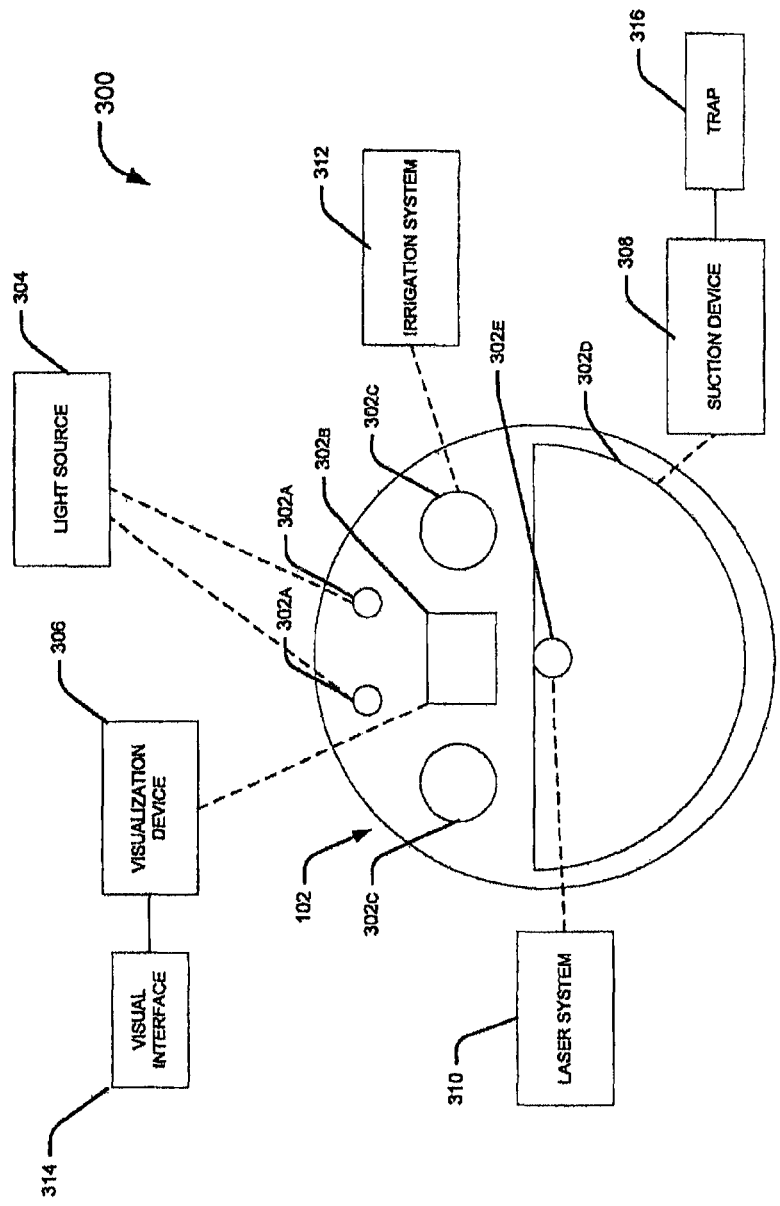
FIG. 3B is a cross-sectional view of an alternative exemplary embodiment of the retrieval device, taken along plane A-A.

FIGS. 3A and 3B illustrate a cross-sectional view of an alternative embodiment of tube 102 (taken along plane A-A' in FIG. 1) depicting multiple channels. As shown in FIG. 3A, tube 102 may include illumination channels 302a, visualization channel 302b, working channels 302c, and return channel 302 (collectively referred to as channels 302). It should be understood that channels 302 may be similar to channels 110, shown in FIG. 1; for description purposes, however, these channels are discussed with specific names.

As shown in FIG. 3A, illumination channels 302a may be connected to a light source 304; visualization channel 302b may accommodate a visualization device 306; return channel 302d may induce a suction force using a suction device 308; and the working channel may accommodate a morcellating device 310, an irrigation system 312, or any other suitable devices, depending on the surgical procedure. As shown, tube 102 may include well-defined channels for various devices and may include a return channel 302d to evacuate excised tissue masses. The illustrated embodiment depicts devices required to perform prostatectomy, for example. It should be understood that the medical devices inserted into channels 302 may vary based on the surgical procedure performed by retrieval device 100.

In general, channels 302 may be defined as elongate hollow lumens that extend, at least partially, between proximal end 104 and distal end 106 of tube 102. Each channel may allow at least one elongate medical device to extend from proximal end 104 to distal end 106, and thus, the diameter of channel 302 may vary accordingly. As shown, return channel 302d may be the largest channel, allowing convenient evacuation of a mass.

The number of channels and their configuration may vary depending on the intended use of the system and the tools required during a procedure. While six channels are illustrated in FIG. 3A, for example, fewer channels or more channels are also contemplated. For example, tube 102 may include a single channel configured to extract a mass from a body, and the channel may also be adapted to receive multiple tools.

Further, channels 302 may have any suitable cross-sectional configuration. For example, as shown, each of channels 302a and 302c may have a substantially circular cross-sectional configuration, while channel 302b may have a square cross-sectional configuration. Moreover, return channel 302d may have a semi-circular configuration. In some embodiments, however, one or more of channels 302 may have a cross-sectional configuration that corresponds to a configuration of a particular tool. In this manner, a particular channel may be specifically designed and dedicated for use with a particular tool.

In addition, although the depicted embodiments illustrate that channels 302 include substantially uniform cross-sectional configurations and dimensions, the cross-sectional dimensions and/or configurations of any of channels 302 may vary as desired. For example, a proximal portion of channel 302 may include a hexagonal cross-sectional configuration, while a distal portion of channel 302 may include a rectangular cross-sectional configuration. In another embodiment, return channel 302d may taper towards a narrower distal end opening. Such tapering may allow only a particular sized mass to enter return channel 302d, reducing clogging of extracted mass within the channel.

Channels 302 may be flexible, semi-rigid, or rigid. Rigidity of channels 302 may generally depend on that of tube 102. In one embodiment, tube 102 may be rigid; however, internal channels 302 may be flexible to accommodate incoming devices. That is, any of channels 302 may be selectively expanded with the insertion of a medical device larger than the channel. Further, one or more channels 302 may include optical fibers. Alternatively, channels 302 may be made of any suitable material, such as, e.g. rubber, fiber, stainless steel. Channels 302 may include sealing mechanisms, such as seals or gaskets, for example, that may enable an incoming medical device to fit into the channel. In addition, an inner surface of any of channels 302 may also include a lubricous coating that allows passage of incoming devices such as, e.g., a camera.

Visualization device 306 may advance into, e.g., visualization channel 302b, via visualization port 116a and may extend out from a distal end opening of channel 302b. In addition, a visual interface 314 may be connected proximate visualization port 116a for viewing the surgical site during the procedure. In an embodiment, the visualization device 306 may be an elongated camera, and a display screen at proximal end 104 may present the images captured by the camera. In such implementations, a miniature camera, e.g., as small as 1 mm by 1 mm, may be used. In addition, substantially high-resolution cameras may be employed to capture a view of the surgical site. Alternatively, visualization device 306 may include a telescope having an eyepiece at its proximal end to view the surgical site.

In general, visualization devices may require illumination to capture the target area. Light source 304 connected to illumination port 116b may illuminate the distal portion of tube 102 through illumination channel(s) 302a. In one embodiment, an optical fiber may be advanced into illumination channel 302a, allowing light to pass through. Alternatively, illumination channel 302a may itself be an optical fiber directly connected to light source 304.

Morcellating device 310 may be used to fragment a mass when inserted into working channel 302c via working channel port 116c. This device may extend along the length of working channel 302c and outward from distal end 106. In one embodiment, the morcellating device may also perform the step of enucleating the undesired mass from the body part.

A laser system may act as morcellator 310. The laser system may direct laser energy through the working channel, and this energy may be directed outward from distal end 106 longitudinally or laterally, as desired. The laser may not only separate the mass from the body, but it may also break the mass down into smaller pieces. The laser device may be positioned at the proximal end of an optical fiber extending through working channel 302c. Alternatively, the channel may itself be an optical fiber that allows passage of laser beams. A laser system may utilize a laser fiber operating at a wavelength ranging from approximately 200 to approximately 500 microns, for example, according to the desired purpose. Various laser systems may include holmium lasers, erbium lasers, KTP, Thulium, or Nd:Yag lasers. In one embodiment, holmium lasers may have a high peak pulse.

Alternatively, morcellating device 310 may be any known tissue or mass cutting device, such as a cautery device or a blade, for example. Those skilled in the art will understand that any device suitable for morcellating tissue may be used in accordance with the present disclosure.

In addition, suction device 308 may withdraw the morcellated mass from the body through, e.g., return port 116e via return channel 302d. As shown, return channel 302d may be the largest channel of tube 102, allowing minimum blockage of retrieved mass while extraction. As already discussed, channels 302d of tube 102 may be designed such that return channel 302d is suitable to extract large pieces of a mass from a body. For extraction, the distal end of return channel 302d may be connected to suction device 308, which may be a vacuum source such as a mechanical pump, for example. In addition, suction device 308 may be connected to a trap 316, which may be a container or a bag, to collect mass and fluids aspirated from the patient. Furthermore, suction device 308 may also be connected to a control that regulates the suction force induced, restricting the force with which the morcellated mass is extracted. Suction device 308 may induce a suitable amount of force so as to avoid harming other body parts. In an alternate embodiment, mechanical structures, such as a grasper or clamp, e.g., that can grasp the morcellated mass may also be inserted into the working channel to retrieve morcellated masses.

Suction device 308 may be employed in connection with irrigation system 130. Working port 116c, connected to one of working channel 302c, may allow a fluid to be directed towards the surgical site through the channel. Irrigation may be used to clean the surgical site during the surgical procedure. In addition, irrigation may maintain a clean environment for the procedure and a clear field of view for the surgeon. For this purpose, a suitable fluid, such as saline water, may be employed. The suction device may aspirate the morcellated mass along with the irrigation fluid.

In addition to the devices discussed above, various other devices may also be introduced depending on the desired procedure. In one embodiment, various biopsy devices, baskets, or other suitable instruments, may also be introduced.

As shown, embodiments of the present disclosure may facilitate an all-in-one retrieval device 100 that not only retrieves an undesired mass from a body, but may also morcellate the mass, illuminate and irrigate the surgical site, and provide images of the surgical site. Device 100 may include a single tube having a wide return channel and one or more additional channels for inserting other medical devices to accomplish additional functionalities. FIG. 3A shows one such embodiment of tube 102 having channels 302 to facilitate this purpose. Those in the art will understand that a range of alternatives could be highlighted to support alternate implementations of the retrieval device 100. For example, morcellator device 310 may not pass through working channel 302c; instead, it may be inserted into return channel 302d. The illumination may be provided by a single channel as opposed to the two channels, as depicted in FIG. 3A.

FIG. 3B illustrates a cross-sectional view of an alternative embodiment of tube 102, taken along line A-A in FIG. 1. Some of the channels depicted in FIG. 3B may be similar to the embodiment shown in FIG. 3A, such as illumination channels 302a, visualization channel 302b, and working channel 302c. These elements may operate in a similar fashion and thus require no further elaboration. In addition, the illustrated embodiment may include a laser fiber 302e introduced into return channel 302d for morcellating purposes. As shown, laser fiber 302e may be securely affixed to a surface of channel 302d.

Laser fiber 302e, directing a laser beam towards the mass, may not only morcellate the mass, but may also assist in enucleating the mass from the body prior to morcellation. As laser fiber 302e is inserted into return channel 302d, working channel 302c may be utilized to introduce other desired devices within the body. Alternatively, one of the working channels may be removed to increase the cross-sectional area of return channel 302d.

In one embodiment, channels 302 may be coupled to metallic tip 202, shown in FIG. 2, of tube 102 using known securing mechanisms. In one embodiment, UV-cured material or resin, e.g., may be deposited along the inner surface of channel 302 within tube 102 to secure tip 202 therein. In such implementations, a significant amount of resin material may be deposited around laser fiber 302e to narrow the distal end opening of channel 302d. Narrowing the opening may allow only tissue pieces smaller than the diameter of return channel 302d to enter tube 102, decreasing the opportunity for those pieces to clog tube 102.

Various alternatives to narrow the distal end opening of return channel 302d may be contemplated. In one embodiment, return channel 302d may itself taper at its distal end. Alternatively, a selectively expandable member, such as a balloon, e.g., may be coupled to the distal inner circumference of return channel 302d. This expandable member may reduce the size of the distal end opening of return channel 302 once tube 102 is deployed at the desired location. In another embodiment, a distal inner surface of return channel 302d may include projections or protrusions that decrease the size of the opening. Further, a mesh-like structure having a desired cell size may be connected to the distal end opening of return channel 302d, allowing a mass smaller than the cell size to enter tube 102. In some embodiments, the distal end opening of return channel 302 may be selectively controllable by a user using a known control mechanism. In such embodiments, the control mechanism may provide suitable feedback to inform the user of the distal end opening's size, and subsequently, the size may be modified, as desired.

In an alternate embodiment, tube 102, along with the channel 302, may be made of resilient materials that expand when a device is inserted into them. For example, visualization channel 302b could expand to fit snuggly around the elongate camera, thereby providing a seal against the ingress of body fluids and materials. In addition, channels 302 may expand, once deployed, permitting entry of large-sized devices.

In another embodiment, channels 302 and/or tube 102 may be made of discrete sections movably linked to one another. Each section may move relative to the adjacent sections, imparting flexibility to channels 302. Discrete sections may be made of a variety of materials, including, for example, a metal, a non-metal, or a shape memory metal, such as nitinol.

Figure 4:
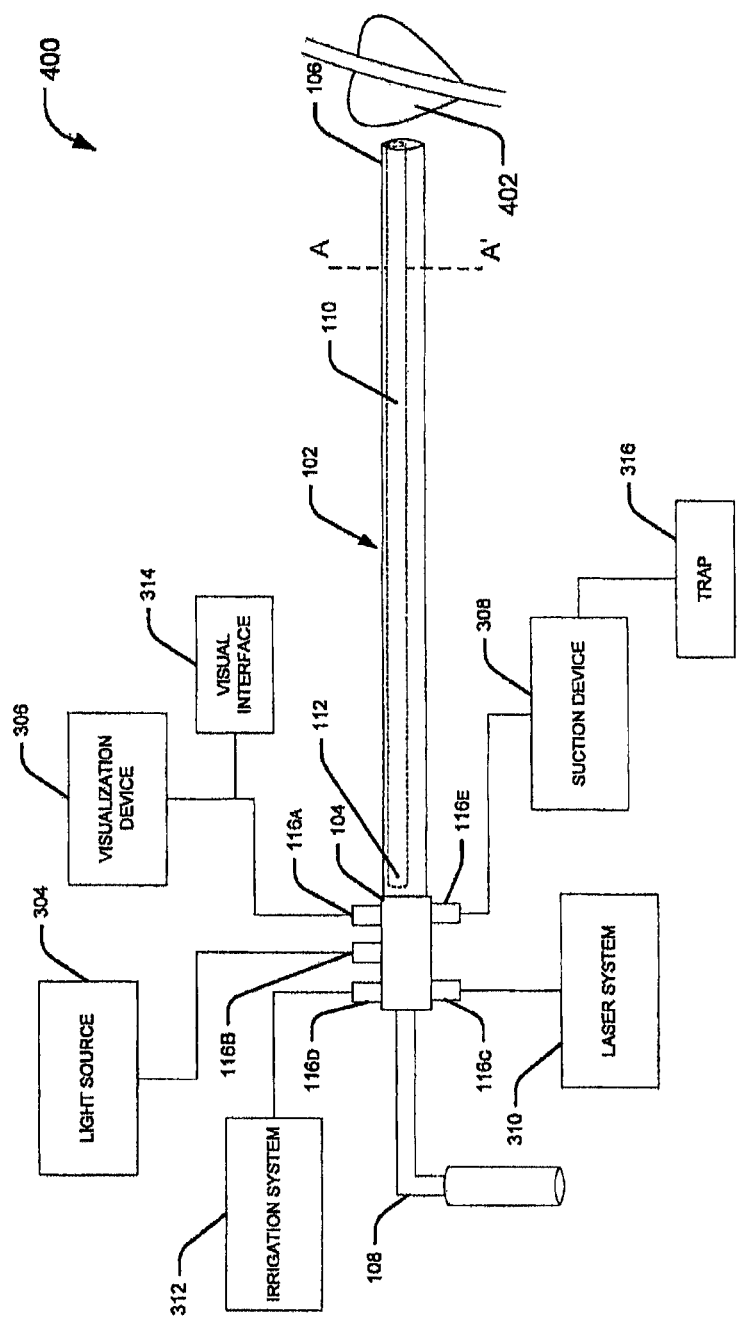
FIG. 4 illustrates exemplary embodiments of the present disclosure including a method of using the system to perform a surgical procedure.

FIG. 4 illustrates a method of using retrieval device 100 according to an embodiment of the present disclosure. The following section describes the implementation of retrieval device 100 in prostatectomy, a procedure to remove prostate 402 from the urinary system. Further, the embodiment of the present disclosure may employ a laser system, such as morcellator device 310. It should be apparent that embodiments of this method may be applicable to a variety of surgical procedures, and a number of the medical devices alluded to above may be employed for resecting the undesired mass.

As tube 102 includes multiple channels to insert the required medical devices, retrieval device 100 may be operated without utilizing an introducer device, such as an endoscope of a cystoscope. Those skilled in the art will understand that the size and configuration of the introducer's working channels may limit the cross-sectional diameter of a return channel for extracting the morcellated prostate from the body. Here, because retrieval device 100 is an all-in-one device, a wider passage may be available for return channel 302d.

As shown, proximal end 104 of tube 102 may be connected to various devices to perform prostatectomy using ports 116. Visualization port 116a may be connected to visualization device 306 such as, e.g., a camera, and illumination port 116b may be connected to light source 304. Working ports 116c and 116d may be connected to a laser system 310 and an irrigation system 312, respectively. In addition, return port 116e may be attached to suction device 308. As already discussed, laser system 310 may introduce laser fiber 302e either into a channel, such as working channel 302c, or may be inserted into return channel 302d.

Under a method of the present disclosure, retrieval device 100 may be inserted into the patient's body. For insertion purposes, distal end 106 of tube 102 may include an atraumatic, rigid, leading edge that may be inserted percutaneously into the urinary system. Alternatively, a slanted tip 202 may allow percutaneous insertion of tube 102. In some embodiments, tube 102 may be introduced via a catheter or with the aid of guide wires or any suitable device that may allow insertion of tube 102.

Tube 102 may be inserted into the body of a patient until distal end 106 is adjacent prostate 402. Distal end 106 of tube 102 may be manipulated to advance towards the surgical location or for repositioning. In one embodiment, the flexible characteristics of tube 102 may allow for maneuvering along the body lumens. Alternatively, an external manipulation mechanism may guide tube 102 towards a target site. For example, distal portion of tube 102 may be connected to pull wires, which may extend up to proximal end 104 for manipulation. Pull wires may be retracted to deflect distal end 106 left or right and/or upward or downward. Pull wires may be controlled manually by a clinician, or an electronic controller may operate the wires. In one embodiment, multiple pull wires may be attached to tube 102 to deflect tube 102 in multiple directions at multiple points along its length. Appropriate positioning of tube 102 may also be accomplished using visualization device 306 inserted into visualization channel 302b.

Once distal end 106 of tube 102 reaches close to prostate 402, the medical devices, such as, e.g., a laser system, a suction source, an irrigation source, etc, may be advanced through one or more channels 302.

To begin a prostatectomy, a laser system may be activated and the targeted prostate tissues may be incised using laser energy. The targeted prostatic tissue may be incised and separated from the body either in its entirety, or in pieces. It may be preferable to incise the targeted prostatic tissue in its entirety to minimize the number of incisions made during the procedure. The surgeon may continue viewing the surgical location using the visualization device. Further, the distal end of tube 102 may be maneuvered along the prostate walls during this process. Irrigation system 130 may be activated to clear the surgical site.

The excised pieces of prostatic tissue may then be pushed into the bladder either by the irrigation fluid exiting the working channel 302c, or by manually pushing the tissue with a distal end of tube 102. Alternatively, suction device 308, attached to retrieval device 100, may hold the prostate pieces close to distal end 106 and retrieval device 100 may then advance into the bladder to deposit the prostate pieces. The bladder may provide a relatively large space for morcellation of the prostate tissues, and may reduce the risk of damaging adjacent tissue. The surgeon may then reposition the distal end of tube 102 toward the center of the bladder, where it may be safe to break down prostate tissues. Alternatively, retrieval device 100 may not reposition the prostate gland tissue to the bladder and these tissues may be morcellated and extracted from their current location.

Next, laser fiber 302e may direct optical energy to fragment prostate tissues into smaller pieces. It should be understood that any suitable morcellating device may replace laser fiber 302e without departing from the scope of the present disclosure. Simultaneously, irrigation system 312 and suction device 308 may be activated to provide irrigation and aspiration (suction) at the distal end. The reciprocating action of irrigating the surgical site together with the aspiration from suction device 308 may efficiently resect the targeted prostatic tissue (cut into smaller pieces by laser system) from the patient. Prostate tissue pieces smaller than the cross-sectional size of return channel 302d may be withdrawn through channel 302d. In one embodiment, return channel 302d may taper along the distal end to reduce coagulation of tissues within the channel. Once tissue is fully aspirated out of the patient, the medical devices may be deactivated, and tube 102 may be pulled out of the body.

This description contemplates a primarily manual operation of the disclosed method. As known in the art, a number of automation techniques may be applied, for example, to improve control and accuracy of the process. For example, the exact amount and intensity of laser may be monitored by a control mechanism, or the penetration itself may be carried out under computer control.

The present disclosure discloses a system that allows resection of masses from a patient's body through natural orifices or incisions. The system may employ a tube having channels that facilitate morcellation along with resection, visualization, irrigation and any additional capabilities.

Other embodiments of the disclosure will be apparent to those skilled in the art from consideration of the specification and practice of the embodiments disclosed herein. It is intended that the specification and examples be considered as exemplary only, with the true scope and spirit of the invention being indicated by the following claims.

What is claimed is:

1. A medical device for extracting tissue, the device comprising:
   an elongate member having a proximal end and a distal end;
   two or more channels extending through the elongate member from the proximal end to the distal end, wherein one of the two or more channels is a return channel configured for extracting resected tissue; and
   a resection device configured to resect tissue wherein the resection device is a laser fiber directly secured to an inner surface of the return channel and remains in a rotationally and axially fixed location relative to the elongate member.

2. The device of claim 1, wherein the elongate member is flexible.

3. The device of claim 1, wherein the elongate member is rigid.

4. The device of claim 1, further including a metallic tip secured to a distal end of the return channel.

5. The device of claim 4, wherein the metallic tip includes a lumen configured to pass resected tissue therethrough and having an inner diameter smaller than that of an inner diameter of the return channel.

6. The device of claim 4, wherein the laser fiber is secured to an inner surface of the metallic tip with a resin that occupies a portion of an inner diameter of the metallic tip.

7. The device of claim 1, wherein the distal end of the elongate member includes a metallic tip.

8. The device of claim 1, wherein the return channel is operably coupled to a suction device.

9. The device of claim 1, wherein the return channel is tapered at the distal end.

10. The device of claim 1, further including a visualization device in one of the two or more channels.

11. The device of claim 1, further including a light source carried in one of the two or more channels.

12. An apparatus for extracting tissue, the apparatus comprising:
    an elongate member having a proximal end and a distal end;
    a plurality of channels extending through the elongate member from the proximal end to the distal end, wherein one of the plurality of channels is a return channel configured for extracting resected tissue and wherein a laser fiber configured to resect tissue is directly secured to an inner surface of the return channel and remains in a rotationally and axially fixed location relative to the elongate member, and wherein the plurality of channels include differing configurations;
    a visualization device configured to observe the tissue in one of the plurality of channels other than the return channel; and
    a light source configured to illuminate tissue, carried in one of the plurality of channels other than the return channel.

13. The apparatus of claim 12, wherein the return channel is operably coupled to a suction device for extracting resected tissue.

14. The apparatus of claim 12, wherein the distal end of the elongate member includes a rigid tip.

15. The apparatus of claim 14, wherein the laser fiber is secured to an inner surface of the rigid tip with a resin that occupies a portion of an inner diameter of the rigid tip.

16. The apparatus of claim 14, wherein the rigid tip includes a lumen configured to pass resected tissue therethrough and having an inner diameter smaller than that of an inner diameter of the return channel.

17. The apparatus of claim 12, further comprising an irrigation system carried in one of the plurality of channels.

* * * * *